US011123318B2

(12) United States Patent
Reiner et al.

(10) Patent No.: US 11,123,318 B2
(45) Date of Patent: Sep. 21, 2021

(54) SUBSTANTIALLY SODIUM FREE DICLOFENAC POTASSIUM ORAL SOLUTIONS

(71) Applicant: APR APPLIED PHARMA RESEARCH S.A., Balerna (CH)

(72) Inventors: Giorgio Reiner, Como (IT); Alberto Reiner, Como (IT); Paola Maffei, Bologna (IT)

(73) Assignee: APR Applied Pharma Research S.A., Balerna (CH)

( * ) Notice: Subject to any disclaimer, the term of this patent is extended or adjusted under 35 U.S.C. 154(b) by 0 days.

(21) Appl. No.: 16/526,365

(22) Filed: Jul. 30, 2019

(65) Prior Publication Data

US 2020/0093772 A1    Mar. 26, 2020

Related U.S. Application Data

(63) Continuation of application No. PCT/IB2018/050505, filed on Jan. 27, 2018.

(30) Foreign Application Priority Data

Jan. 30, 2017    (IT) .................. 102017000009711

(51) Int. Cl.
*A61K 31/196* (2006.01)
*A61P 29/00* (2006.01)
*A61K 9/08* (2006.01)

(52) U.S. Cl.
CPC .............. *A61K 31/196* (2013.01); *A61K 9/08* (2013.01); *A61P 29/00* (2018.01)

(58) Field of Classification Search
CPC .......... A61K 31/196; A61K 9/08; A61P 29/00
See application file for complete search history.

(56) References Cited

U.S. PATENT DOCUMENTS

2016/0213784 A1* 7/2016 Kisak ..................... A61K 47/34

FOREIGN PATENT DOCUMENTS

WO    WO 1997/044023    * 11/1997
WO    WO 2013/052019    * 11/2013

* cited by examiner

*Primary Examiner* — Sahar Javanmard
(74) *Attorney, Agent, or Firm* — Sterne, Kessler, Goldstein & Fox P.L.L.C.

(57) ABSTRACT

Provided are orally formulations of diclofenac potassium with improved stability in response to cold conditions, and excellent taste and palatability.

15 Claims, 5 Drawing Sheets

SUBSTANTIALLY SODIUM FREE DICLOFENAC POTASSIUM ORAL SOLUTIONS

FIELD OF THE INVENTION

The present invention relates to liquid compositions for oral use comprising substantially sodium-free diclofenac potassium salt. According to the present invention, the term "substantially sodium-free" indicates a composition where the sodium is absent or present in a maximum amount of 0.05% expressed as grams of sodium per 100 ml of solution.

BACKGROUND OF THE INVENTION

Diclofenac is a non-steroidal anti-inflammatory drug (NSAID), used in the treatment of various painful inflammatory conditions. From the clinical point of view, diclofenac is endowed with analgesic, anti-inflammatory and antipyretic properties, especially in the case of low-dose administration.

Its mechanism of action involves the inhibition of the prostaglandin synthase enzyme and therefore the competitive inhibition of prostaglandin biosynthesis, the (partial) inhibition of lysosomal enzymes, the non-selective inhibition of COX-1 (cyclooxygenase-1) and COX-2 (cyclooxygenase-1) and the inhibition of 5-LO (5-lipoxygenase). Diclofenac is also able to inhibit the release of arachidonic acid by phospholipases, and in certain cases it stimulates reabsorption of arachidonic acid.

Diclofenac is generally taken by the oral route, in the form of immediate release tablets or tablets covered with gastro-resistant coatings, although it is also taken by the rectal, parenteral, ophthalmic and topical routes. The possibility of taking diclofenac as candies, melting tablets, coated tablets, chewing gum or other similar pharmaceutical forms, or in formulations for the extemporaneous preparation of aqueous solutions and/or suspensions, would represent a similar route but would require a different formulation. These new dosage forms could definitely be more suitable for some populations such as the elderly who have difficulty swallowing.

From the pharmacokinetic point of view, after oral administration diclofenac is completely absorbed through the gastrointestinal tract. After absorption, it is rapidly distributed to the tissues and the peak plasma level is reached within 1 hour. Diclofenac extensively binds to plasma proteins (99.7%) and in particular to albumin. It is metabolized in the liver, where it is glucoronidated and undergoes first pass metabolism. About 60% of the administered dose is eliminated as the metabolite by the renal route (less than 1% is excreted as unchanged substance). About 30% of the administered dose is excreted in the bile and in the faeces.

Diclofenac is 2-(2-[2,6-diclorofenilammino] phenyl) ethanoic acid and has the following structural formula.

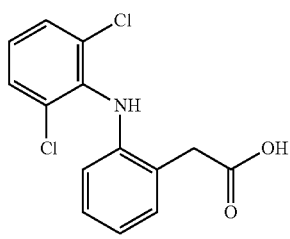 [SMILES: O=C(O)Cc1ccccc1Nc1c(Cl)cccc1Cl]

Diclofenac has a low solubility in water and therefore is normally used in a salified form.

Customary diclofenac salts are those of alkali metals and alkaline-earth metals, such as sodium and potassium, together with those of organic nature, like the salts of basic amino acids such as lysine, arginine and ornithine and other pharmacologically acceptable organic bases, which can make the resulting salt soluble in water.

Pharmaceutical compositions for oral use of diclofenac are generally known for some side effects related to the palatability of the active principle. Diclofenac salts are in fact characterized by a particularly unpleasant and bitter taste and by the fact that they give a sensation of strong astringency and generate a particularly intense tingling in the oral cavity, especially in the area of the larynx. These issues can be solved by adding flavourings or sweeteners that are able to cover the bitter taste of the formulation, thus making pleasant the taking of the oral preparations. As regards the problems linked to the tingling and the sensation of strong astringency, the market presently offers products comprising in their solution carbonates and bicarbonates of alkali metals or alkaline earth metals composing the diclofenac salt, which significantly reduce the problems set forth above.

Various documents have described liquid formulations of diclofenac used for the treatment of pain. In the United States, liquid solutions of diclofenac are approved for topical, ophthalmic and parenteral administration. See, e.g., FDA-approved prescribing information for Dyloject® 37.5 mg/ml intravenous solution, Voltaren® 0.1% ophthalmic drops, and Pennsaid® 1.5% topical solution. WO 97/44023 also describes liquid diclofenac solutions for oral administration.

In Europe, a liquid solution is approved for oral administration based on the formulations described in EP1159960B1. This document discloses a pharmaceutical composition for oral use containing diclofenac in the form of sodium or potassium salt in admixture with sodium or potassium bicarbonate, which allows one to obtain a product with a reduced astringent sensation in the area of the larynx. The liquid formulations for oral use can show formation of precipitate at low temperatures, such as temperatures lower than 5° C., which are normal temperatures in winter season. Therefore there is a need for additional formulations that remain stable under cold conditions, particularly during the winter period in the warehouse or during transport.

The stability of the product is particularly relevant for its administration to the patient without any alteration, both from the chemical-physical point of view and from the organoleptic point of view. Furthermore, a pharmaceutical composition must be easily transportable and storable without running the risk of deterioration of the product.

In light of all the above considerations, it would be advantageous to provide a liquid pharmaceutical composition for oral use having pleasant organoleptic characteristics, for easy acceptance by the patient.

It would also be advantageous to have a liquid pharmaceutical composition for oral use that is stable and lasting, even at low temperatures.

SUMMARY OF THE INVENTION

In a first principal embodiment, the invention provides a liquid pharmaceutical composition for oral use, characterized by comprising: (a) diclofenac potassium salt in an amount from 3.5 to 20% (w/v) with respect to the volume of the composition; and (b) potassium bicarbonate in an amount from 2.0 to 10.0% (w/v) with respect to the volume of the composition; wherein the sodium is absent or present in an amount of up to 0.05% by weight with respect to the volume of the composition.

In a second principal embodiment, the invention provides a liquid pharmaceutical composition for oral use, characterized by comprising: (a) diclofenac potassium salt in an amount from 3.5 to 20% (w/v) with respect to the volume of the composition, and (b) potassium bicarbonate in an amount from 2.0 to 10.0% (w/v) with respect to the volume of the composition with a density ranging between 0.5 and 2 g/L.

In a third principal embodiment, the invention provides a liquid pharmaceutical composition comprising: (a) about 5 weight parts diclofenac potassium, (b) about 30 weight parts ethyl alcohol, (c) about 20 weight parts glycerol, (d) about 2.5 weight parts potassium hydrogen carbonate, (e) about 0.5 weight parts sucralose, (f) about 42.9 weight parts water, and optionally about 0.00336 weight parts E129 and about 0.000168 weight parts E133.

In a fourth principal embodiment, the invention provides a kit for the administration of an oral drug solution comprising: (a) a vial in which is house a defined amount of the composition of any of the principal embodiments or subembodiments of the present invention; and (b) a dropper apparatus or graduated pipette.

In a fifth principal embodiment, the invention provides a method of treating pain comprising administering a therapeutically effective amount of the composition of any of the principal embodiments or subembodiments of the present invention to a patient in need thereof.

In a sixth principal embodiment, the invention provides a method of making a liquid formulation of diclofenac potassium comprising: (a) preparing a first mixture comprising diclofenac potassium and ethanol; (b) mixing water and glycerol in said first mixture until a second mixture is obtained; (c) preparing a third mixture comprising water, potassium hydrogen carbonate, and sucralose; and (d) mixing the third mixture and second mixture and adding water to make a final mixture.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the invention.

DETAILED DESCRIPTION

Figure 1:
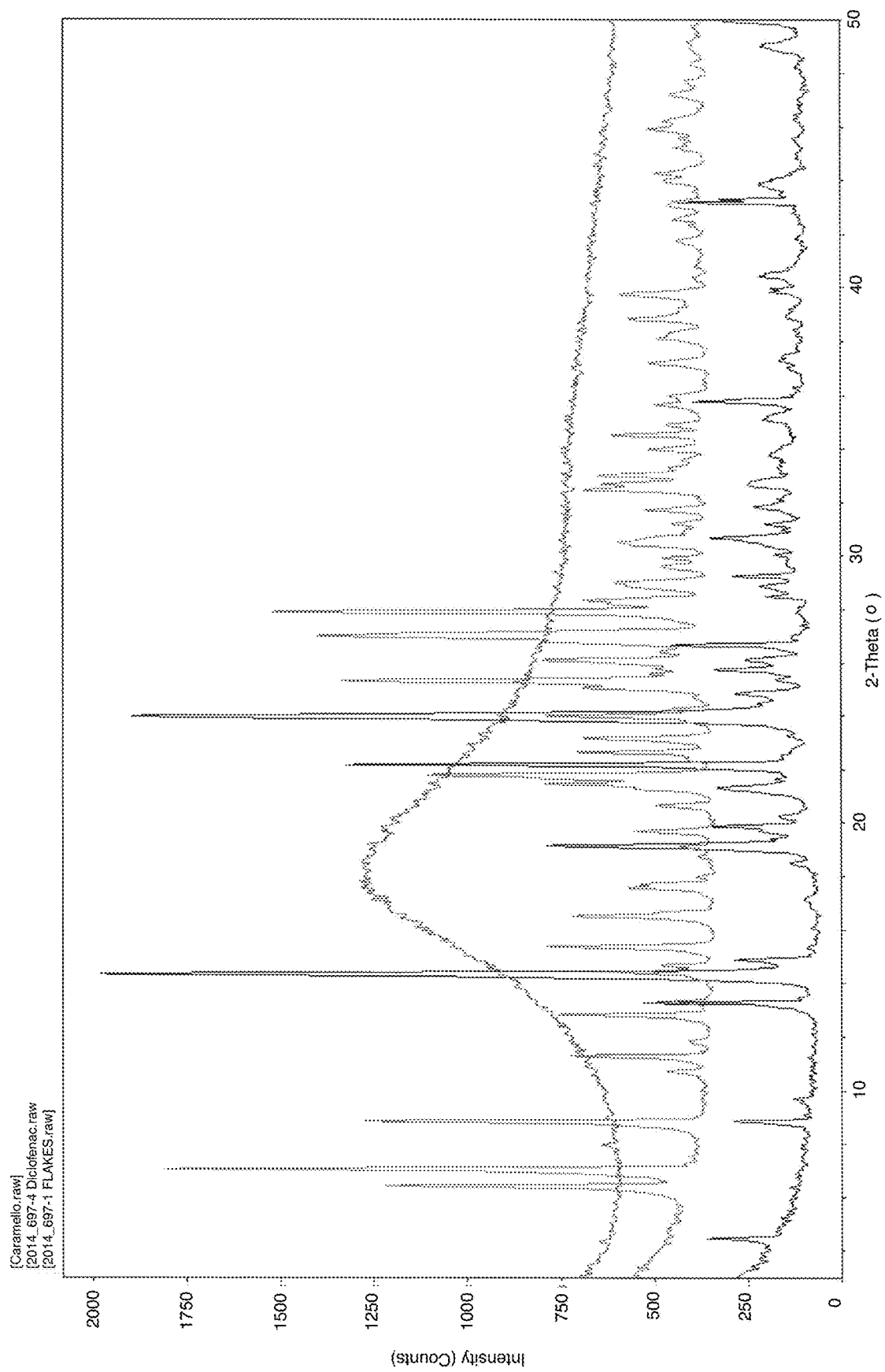
FIG. 1 is an X-ray diffraction spectrum of the precipitate observed in the diclofenac potassium formulation reported in Example 1.

The pharmaceutical composition according to the present invention is a pharmacologically active composition of diclofenac for oral use that is well accepted by the patient from an organoleptic point of view and that, at the same time, allows for easy storage and transport while maintaining unchanged the physico-chemical characteristics of the product. According to the present invention, the liquid pharmaceutical composition for oral use is an oral solution at a concentration preferably at 50 mg/ml, optionally in combination with a graduated EC marked pipette that preferably measures 0.5 ml or 1 ml, to be administered in the form of oral solution after dilution with water.

The oral solution is particularly advantageous because it allows administration at low dosage of diclofenac, which can be administered one or more times in a day. The oral solution can be useful for paediatric administration and for patients with deglutition difficulties, who have difficulty swallowing tablets or capsules. The formulation of active principles in the form of oral solutions is also particularly advantageous for its ease of dosing, because the patient can easily dose the drug without running the risk of overdosing or not reaching the effective dose. A diclofenac liquid composition is particularly useful in this regard.

The pharmaceutical composition according to the present invention is preferably defined by a density ranging between 0.5 and 2 g/ml, preferably between 1.0 and 1.1 g/ml, still more preferably between 1.0 and 1.05 g/ml. In this density range, a liquid composition is obtained that can be easily measured with a graduated EC marked pipette.

In order to obtain a dose of pharmaceutically acceptable active principle, the pharmaceutical composition according to the present invention comprises diclofenac potassium salt in an amount of between 1.5 and 20% by weight with respect to the volume of the composition, preferably in an amount of between 3 and 7% by weight with respect to the volume of the composition, still more preferably between 4 and 6% by weight with respect to the volume of the composition.

In order to eliminate or greatly reduce the sensation of astringency and intense tingling in the oral cavity, especially in the area of the larynx, the pharmaceutical composition according to the present invention comprises potassium bicarbonate in an amount between 2 and 10% by weight with respect to the volume of the composition, preferably in an amount between 2 and 5% by weight with respect to the volume of the composition, still more preferably between 2.5 and 3% by weight with respect to the volume of the composition. A composition is thus obtained containing diclofenac in a pharmacologically active amount that eliminates or reduces the problems of palatability set out above, being therefore acceptable for the patient.

In order to avoid the possible precipitation of diclofenac sodium salts at low temperature, the pharmaceutical composition according to the present invention has a maximum concentration of sodium ions of 0.5% by weight with respect to the volume of the composition, preferably lower than 0.1% by weight with respect to the volume of the composition, more preferably lower than 0.05%.

In order to reduce the unpalatable feeling of the pharmaceutical composition due to the bitter taste of diclofenac salts, the pharmaceutical composition according to the present invention comprises at least one sweetening substance substantially free of sodium ions. The aforesaid sweetening substance is present in the composition in amounts ranging between 0.3 and 2.0% by weight with respect to the volume of the composition. The sweetening substance can be selected in the group consisting of: sucralose, aspartame, acesulfame K, thaumatin, isomalt, maltitol, lactitol, xylitol or mixtures thereof.

The pharmaceutical compositions of the present invention may also comprise other pharmaceutically acceptable substances in order to facilitate its preparation or storage or to make the preparation even more pleasant to the patient.

The invention also related to methods for preparing the formulations of the present invention and, in a sixth principal embodiment, the invention provides a method of making a liquid formulation of diclofenac potassium comprising: (a) preparing a first mixture comprising diclofenac potassium and ethanol; (b) mixing water and glycerol in said first mixture until a second mixture is obtained; (c) preparing a third mixture comprising water, potassium hydrogen carbonate, and sucralose; and (d) mixing the third mixture and second mixture and adding water to make a final mixture. The method may further comprise mixing dye Allura Red (E129) and Brilliant Blue (E133) in step (c) to make said third mixture.

Thus, in a sub embodiment of the sixth principal embodiment:
step (a) is carried out with from 100 to 150 weight parts ethanol per 10-30 weight parts potassium diclofenac;
step (b) is carried out with from 60-100 weight parts glycerol and 100-150 weight parts water per 10-30 weight parts potassium diclofenac;
step (c) is carried out with from 40-70 weight parts water, 5-20 weight parts potassium hydrogen carbonate, 1-5 weight parts sucralose per 20 weight parts diclofenac potassium; and
in step (d) water is added in until a 5% w/v solution is obtained based on the weight of potassium diclofenac at a density of approximately from 0.5 to 1.5 g/mL.

The method can also be defined based on the relative weight or volume parts of the ingredients used to make the compositions of the present invention. Thus, in a particular embodiment of the sixth principal embodiment: step (a) is carried out with 120 weight parts ethanol per 20 weight parts potassium diclofenac; step (b) is carried out with 80 weight parts glycerol and 120 weight parts water per 20 weight parts potassium diclofenac; step (c) is carried out with 56.6 weight parts water, 10 weight parts potassium hydrogen carbonate, and 2 weight parts sucralose per 20 weight parts diclofenac potassium; and water is added in step (d) until a 5% w/v solution is obtained based on the weight of potassium diclofenac at a density of approximately 1.030 g/mL. Alternatively, the method may further comprise mixing 0.01344 weight parts dye Allura Red (E129) and 0.00067 weight parts Brilliant Blue (E133) in step (c) to make said third mixture.

The pharmaceutical composition is thus provided that is suitable for the short-term treatment of the following acute disorders:
painful post-traumatic inflammations, e.g. after sprains;
postoperative inflammations and pain, e.g. after dental and orthopaedic operations;
primary dysmenorrhea; and
migraine attack.

The composition according to the invention can be administered one or more times daily: the usually dosage strength is 50 mg of diclofenac potassium salt. The maximum daily quantity is 200 mg of diclofenac.

The pharmaceutical compositions of the present invention are characterized by having a good palatability and well accepted by the subjects.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

The general storage conditions for the stability studies reported in the Examples were the ICH conditions (i.e. 25° C./60% RH and 40° C./75% RH) and the refrigerator temperature was defined by WHO guidance (i.e. 5°±3° C., range 2°-8° C.) and the additional temperature of 8-10° C.

In order to characterize the precipitate reported in the Examples, the content of the bottle with the presence of precipitate was filtered on a 0.45 μm filter; the brownish solid was washed several times with water until it turned to grey. The solid was left to dry at room temperature and then analysed. The analytical methods to characterize the precipitate were: X-Ray Powder Diffraction (XRPD), Differential Scanning calorimetric (DSC), Thermogravimetric Analysis (TGA), Fourier Transform-Infrared/Attenuated Total Reflection (FT-IR/ATR) and SEM-EDX Example 1

Preparation and Stability of Comparative Formulation

Example 1 was performed using a commercially available diclofenac potassium oral solution that corresponds to a commercial formulation in order to evaluate the stability of the formulation. The preparation of a 400 liters solution is as follows:

In a first container, 20.0 kg of diclofenac potassium salt was placed in 120 litres of ethanol and stirred at room temperature for about 15 minutes. 80 kg of glycerol and 120 kg of water were then added to the first container and mixed until a complete dissolution was obtained. In a second container, an aqueous solution consisting of 56.6 kg water, 10.0 kg potassium hydrogen carbonate, 6 kg sodium saccharin and 1 kg caramel E150a, was mixed until a homogenous solution was obtained, and subsequently added to the first solution. The resulting solution was brought to a final volume of 400 litres with water. The final solution, having a density of 1.033 g/ml, was partitioned into 20 and 100 ml glass bottles type III. The composition of each bottle is reported in Table 1.

TABLE 1

| Component | Formulation 1a V = 20 ml | Formulation 1b V = 100 ml | % w/v |
|---|---|---|---|
| Potassium diclofenac | 1.0 g | 5.0 g | 5.0 |

TABLE 1-continued

| Component | Formulation 1a V = 20 ml | Formulation 1b V = 100 ml | % w/v |
|---|---|---|---|
| Ethanol | 6.0 g | 30.0 g | 30.0 |
| Glycerol | 4.0 g | 20 g | 20.0 |
| Potassium hydrogen carbonate | 0.5 g | 2.5 g | 2.5 |
| Sodium saccharin | 0.3 g | 15 g | 1.5 |
| Caramel E150a | 0.05 g | 0.250 | 0.25 |
| Purified water | q.s to 20 ml | q.s to 100 ml | |

Bottles containing the oral solution reported in Table 1 were stored at a temperature between 8 and 10° C. After about 1 month, it was observed that the solution showed a visible precipitate. Bottles of the same composition of Example 1, containing the diclofenac active principle, were maintained at a temperature between 5° C.±3° C. in order to verify the behaviour at the refrigerated temperature. In this condition after 1 day all bottles showed complete precipitation after just 1 day.

Figure 2:
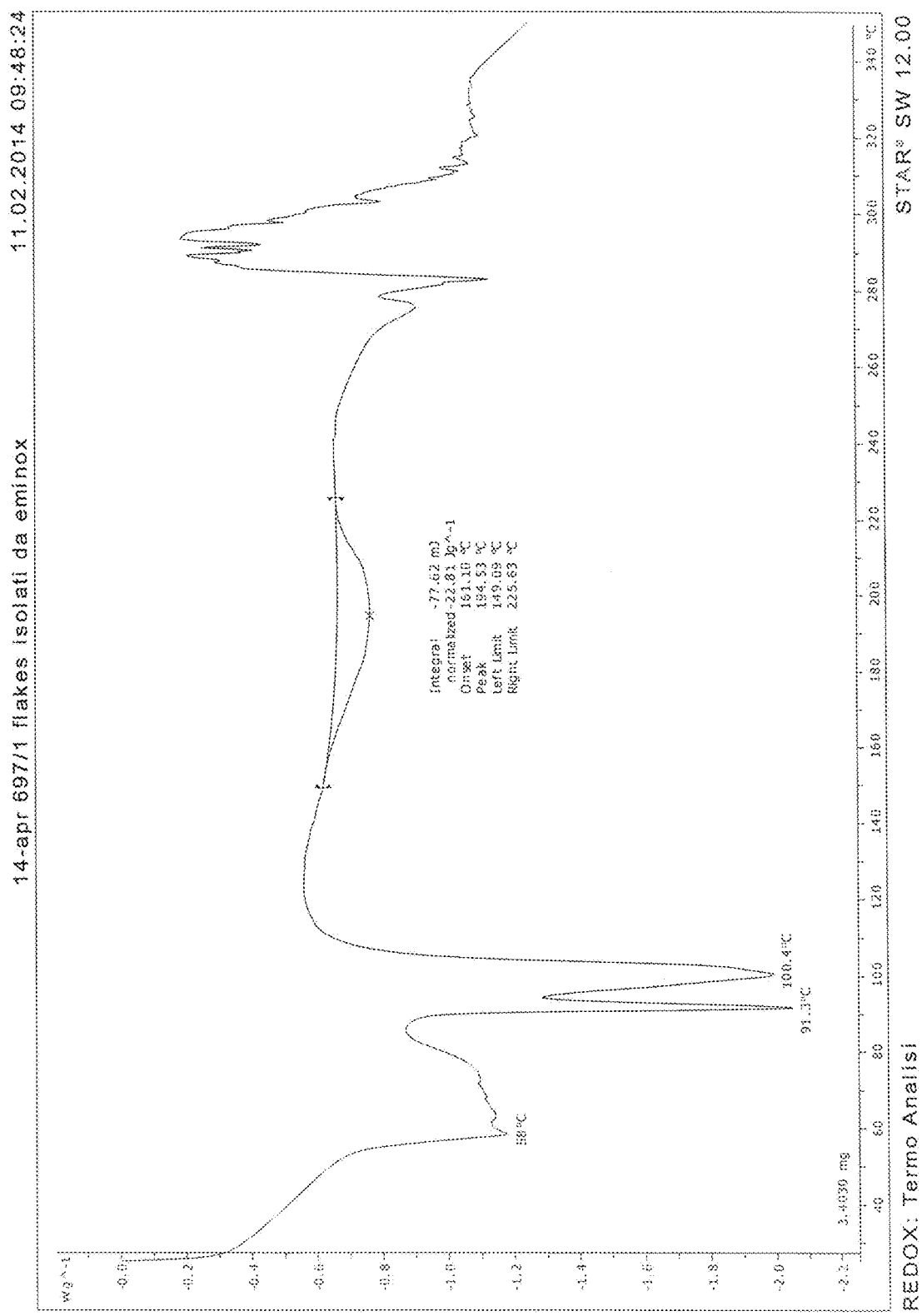
FIG. 2 is a Differential Scanning calorimetric (DSC) spectrum of the precipitate observed in the diclofenac potassium formulation reported in Example 1.
Figure 3:
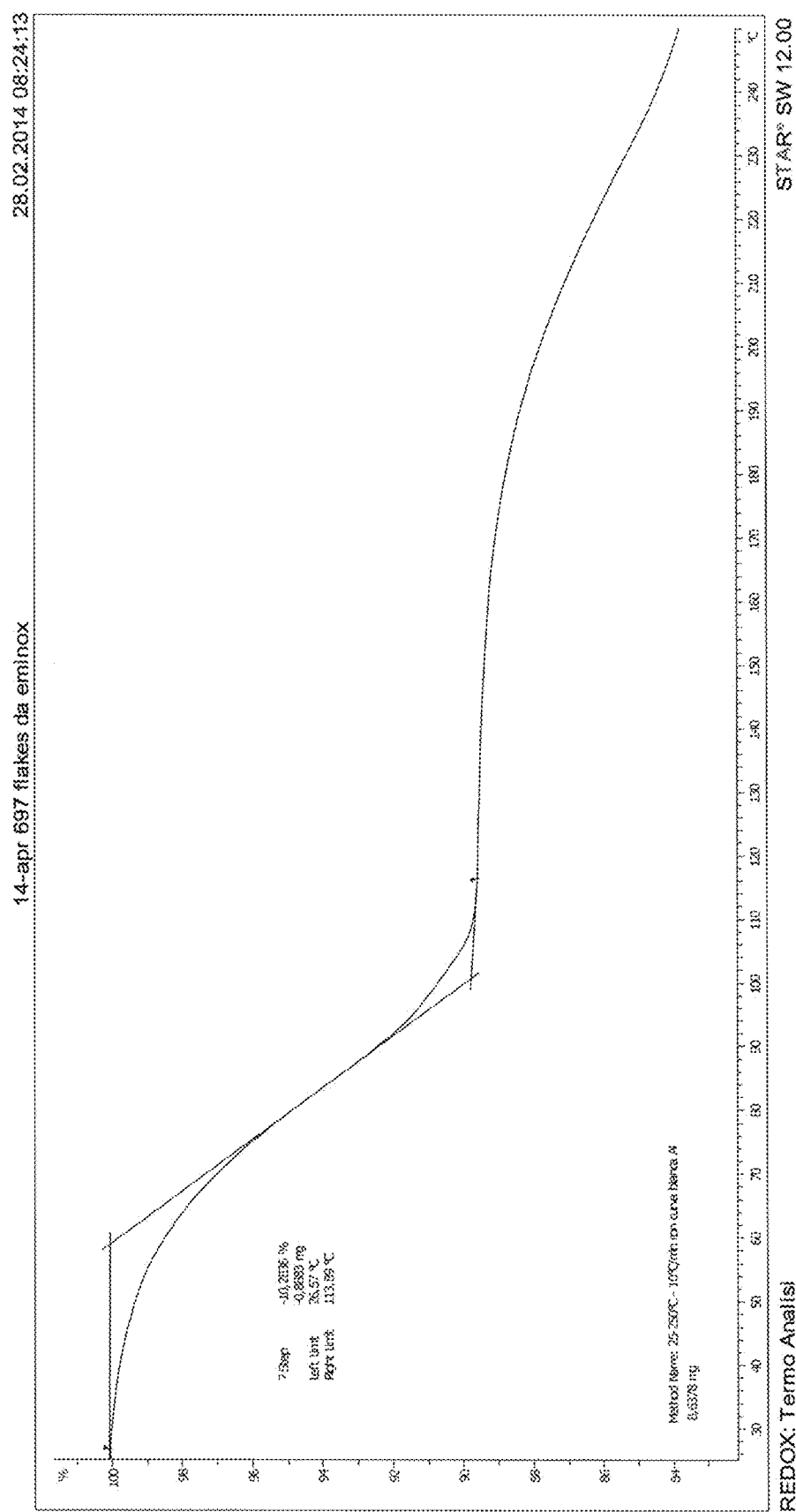
FIG. 3 is a Thermogravimetric Analysis (TGA) spectrum of the precipitate observed in the diclofenac potassium formulation reported in Example 1.
Figure 4:
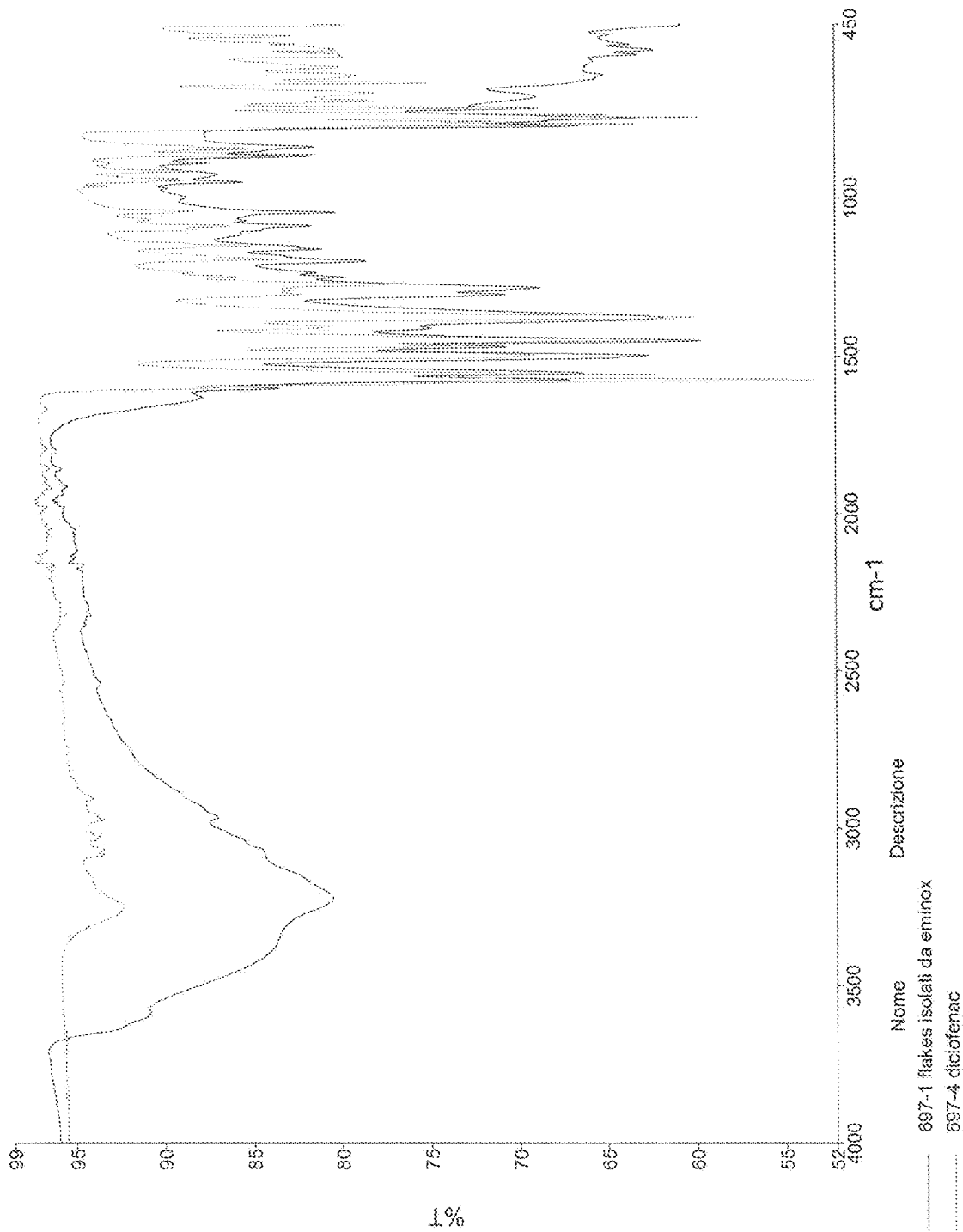
FIG. 4 is a Fourier Transform-Infrared/Attenuated Total Reflection (FT-IR/ATR) spectrum of the precipitate observed in the diclofenac potassium formulation reported in Example 1.
Figure 5:
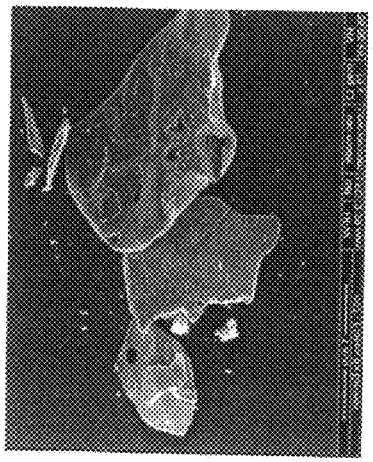
FIG. 5 is a SEM photo plus EDX of the precipitate observed in the diclofenac potassium formulation reported in Example 1.
Figure 5:
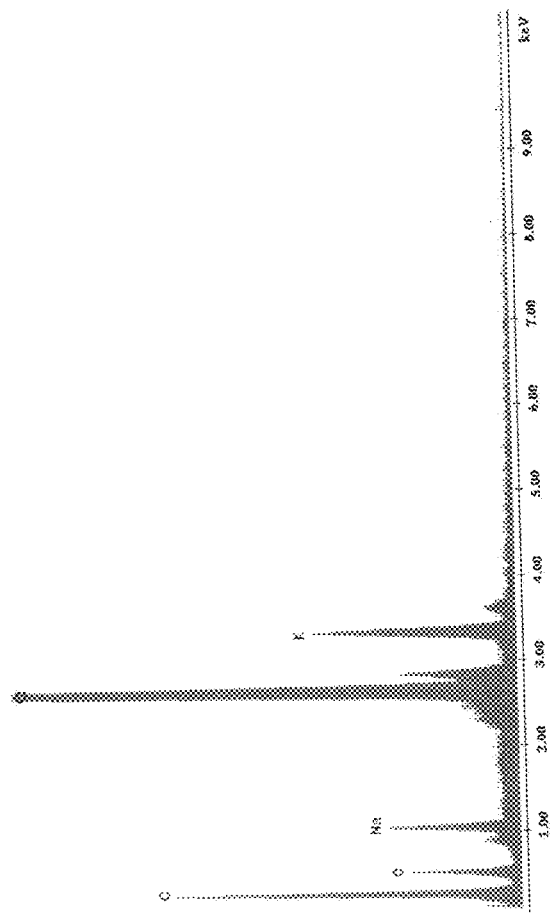

The solution with the presence of precipitate was filtered and the precipitate was characterized by X-ray diffraction using the tool LAST IV (Rigaku), intensity 40 mA, voltage 50 kV. FIG. 1 shows the X-ray diffraction spectrum where it can be seen that the analysed precipitate is a mixture of dihydrate potassium diclofenac and tetrahydrate sodium diclofenac. The solvate polymorphic forms of dihydrate potassium diclofenac and tetrahydrate sodium diclofenac were also analysed by DSC (FIG. 2), TGA (FIG. 3), FT-IR/ATR analysis (FIG. 4), and SEM-EDX (FIG. 5).

Example 2

Preparation and Stability of Inventive Formulation

This example was carried out by making a solution containing diclofenac potassium salt in the presence of a reduced content of sodium ions according to the invention in order to evaluate the stability of new formulations of diclofenac. Preparation of a 400 liters solution is as follows:

In a first container, 20.0 kg of potassium diclofenac was placed in 120 liters of ethanol under stirring at room temperature for about 15 minutes). 80 kg of glycerol and 120 kg of water were then added to the first container and mixed until a complete solution was obtained. In a second container, an aqueous solution consisting of 56.6 kg water, 10.0 kg potassium hydrogen carbonate, 2.0 kg sucralose, 13.44 g dye Allura Red (E129) and 0.67 mg Brilliant Blue (E133) was prepared, and subsequently mixed with the first solution. Water was then added to the solution to bring the final volume to 400 litres. The final solution having a density of about 1.030 g/ml was partitioned into 20 and 100 ml glass bottles type III. The composition of each bottle is reported in Table 2.

TABLE 2

| Component | Formulation 2a V = 20 ml | Formulation 2b V = 100 ml | % w/v |
|---|---|---|---|
| Potassium diclofenac | 1.0 g | 5.0 g | 5.0 |
| Ethanol | 6.0 g | 30 g | 30.0 |
| Glycerol | 4.0 g | 20 g | 20.0 |
| Potassium hydrogen carbonate | 0.5 g | 2.5 g | 2.5 |
| Sucralose | 1.0 g | 0.5 g | 0.5 |
| Allura Red (E129) | 0.672 mg | 3.36 mg | 0.00336 |
| Brilliant Blue (E133) | 0.0336 mg | 0.168 mg | 0.000168 |
| Purified water | q.s to 20.0 ml | q.s to 100.0 ml | |

The bottles containing the diclofenac active principle were maintained at a temperature between 8 and 10° C. After a period of 12 months, the solutions were clear and no bottle showed the presence of precipitate.

The bottles of the same composition of Example 2 containing the diclofenac active principle were maintained at a temperature between 5° C.±3° C. in order to verify the behaviour at the refrigerated temperature. In this condition within 30 days only 1 bottle out of 14 showed the presence of some crystals. At the same temperature, the previous composition in presence of sodium ions, showed completed precipitation just after 1 day and for all bottles. The obtained results clearly show how the diclofenac formulation according to the present invention is "more stable" at low temperature when compared to the one containing sodium saccharin.

Example 3

Evaluation of Effect of Diclofenac Concentration

The example was carried out by making two different solutions containing diclofenac potassium salt at two different concentrations, according to the present invention, in order to evaluate the stability of the composition with different contents of active principle. The compositions were prepared in a volume of 50 ml following the same procedure as in Examples 2.

Table 3 reports the unitary compositions with the respective weight percentages.

TABLE 3

| Component | Formul. 3 | % w/V | Formul. 4 | % w/V |
|---|---|---|---|---|
| Potassium diclofenac | 2.0 g | 4.0 | 3.0 g | 6.0 |
| Ethanol | 15.0 g | 30.0 | 15.0 g | 30.0 |
| Glycerol | 10.0 g | 20.0 | 10.0 g | 20.0 |
| Potassium hydrogen carbonate | 1.25 g | 2.5 | 1.25 g | 2.5 |
| Sucralose | 0.25 g | 0.5 | 0.25 g | 0.5 |
| Allura Red (E129) | 1.8 mg | 0.0036 | 1.8 mg | 0.0036 |
| Brilliant Blue (E133) | 0.084 mg | 0.000168 | 0.084 mg | 0.000168 |
| Purified water | q.s to 50 ml | | q.s to 50 ml | |

The bottles were maintained at a temperature comprised between 8 and 10° C. and after a month the solutions were clear, with no precipitate. The example highlights how the variation of the concentrations of potassium diclofenac did not lead to the formation of precipitates with respect to the solution prepared in Example 2.

Example 4

Determination of the Effect of Sodium Ion Concentration of Stability Formation The example was carried out to assess the minimum amount of sodium ions that would cause precipitation of diclofenac sodium salt. Diclofenac-containing compositions were prepared in a volume of 50 ml in accordance with Example 1 with varying concentrations of sodium saccharin. A series of formulations, whose composition is described in Table 4, were obtained. Table 4 reports the unitary concentrations and percentage amounts of the components.

TABLE 4

| Component | Formul. 5 | Formul. 6 | Formul. 7 | Formul. 8 | Formul. 9 | Formul. 10 | Formul. 11 |
|---|---|---|---|---|---|---|---|
| Potassium diclofenac | 2-5 g (5% w/v) | 2.5 g (5% w/v) | 2.5 g (5% w/v) | 2.5 g (5% w/v) | 2.5 g (5% w/v) | 2.5 g (5% w/v) | 2.5 g (5% w/v) |
| Ethanol | 15 g (30% w/v) | 15 g (30% w/v) | 15 g (30% w/v) | 15 g (30% w/v) | 15 g (30% w/v) | 15 g (30% w/v) | 15 g (30% w/v) |
| Glycerol | 10 g (20% w/v) | 10 g (20% w/v) | 10 g (20% w/v) | 10 g (20% w/v) | 10 g (20% w/v) | 10 g (20% w/v) | 10 g (20% w/v) |
| Sodium saccharin | 0.875 g (1.75% w/v) | 0.75 g (1.5% w/v) | 0.625 g (1.25% w/v) | 0.5 g (1.00% w/v) | 0.375 g (0.75% w/v) | 0.25 g (0.50% w/v) | 0.125 g (0.25% w/v) |
| Potassium hydrogen | 1.25 g (2.5% w/v) | 1.25 g (2.5% w/v) | 1.25 g (2.5% w/v) | 1.25 g (2.5% w/v) | 1.25 g (2.5% w/v) | 1.25 g (2.5% w/v) | 1.25 g (2.5% w/v) |
| Purified water | q.s to 50 ml | q.s to 50 ml | q.s to 50 ml | q.s to 50 ml | q.s to 50 ml | q.s to 50 ml | q.s to 50 ml |
| Sodium concentration | 72.56 mmol/l | 62.19 mmol/l | 51.83 mmol/l | 41.46 mmol/l | 31.10 mmol/l | 20.73 mmol/l | 10.36 mmol/l |

On the solutions corresponding to the formulations 5-11 was performed a stability study at about 10° C. to evaluate the precipitate formation. Table 5 reports the results after a period of 2 months.

TABLE 5

| | Stability at 10° C. | | | | | | |
|---|---|---|---|---|---|---|---|
| | Formul. 5 | Formul. 6 | Formul. 7 | Formul. 8 | Formul. 9 | Formul. 10 | Formul. 11 |
| Check presence of precipitate | Presence precipitate | Presence precipitate | Presence precipitate | Presence precipitate | Presence precipitate | Presence precipitate | Clear solution |

The solutions corresponding to the formulations 5-11 were filtered using 45 micron PVDF filters and the concentration of diclofenac potassium salt in solution was determined by spectrophotometric method at a wavelength of 276 nm. Table 6 reports the obtained concentrations of diclofenac potassium.

TABLE 6

| | Concentration of diclofenac potassium salt in the supernatant of the suspensions or in solution in mg/ml | | | | | | |
|---|---|---|---|---|---|---|---|
| | Formul. 5 | Formul. 6 | Formul. 7 | Formul. 8 | Formul. 9 | Formul. 10 | Formul. 11 |
| Concentration of diclofenac potassium salt | 21.32 mg/ml | 34.38 mg/ml | 37.95 mg/ml | 40.17 mg/ml | 44.31 mg/ml | 46.84 mg/ml | 51.28 mg/ml |

The example shows that at concentrations of sodium saccharin higher than 0.25% w/v the compositions of diclofenac K showed presence of precipitate and the consequent decrease of the concentration of diclofenac K in solution.

Example 5

Determination of the Stability of Inventive Formulation Under Thermal Shock

This example was carried out in order to assess the response of the Formulation 1 and Formulation 2 to sudden temperature changes in relation to their stability. Cooling experiments were performed under stirring conditions.

The solution prepared in accordance with Example 1, maintained at 20° C., was slowly cooled to 5° C. and after 3 minutes a precipitate was observed. The temperature was further lowered to 0° C. and then to −5° C. without observing any further increase of the precipitate with respect to the one obtained at 5° C. The suspension was then brought to 5° C. and no solubilisation of the precipitate was observed. The suspension was then heated to 10° C. and the precipitate did not solubilise.

A solution similar to the Formulation 2 (increasing sucralose concentration to 1% and using yellow E102 as the coloring agent instead of E129+E133) maintained at 20° C., was subsequently cooled to 5° C. and no precipitate was observed. The temperature was further lowered to −5° C. and at this temperature it was observed the formation of a precipitate, which completely solubilised again when the temperature was brought to 10° C. The example shows how the pharmaceutical composition according to the invention is more stable to thermal shock. Available experimental data thus confirm that the compositions according to the invention can advantageously be stored for 12 months at 10° C.

Other embodiments of the invention may be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of making a liquid composition of diclofenac potassium comprising:
   a) preparing a first mixture comprising diclofenac potassium and ethanol;
   b) mixing water and glycerol in said first mixture until a second mixture is obtained;
   c) preparing a third mixture comprising water, potassium hydrogen carbonate, and sucralose;
   d) mixing the third mixture and second mixture and adding water to make a final mixture;
   wherein:
      i) said liquid composition comprises diclofenac potassium salt in an amount from 3.5 to 20% (w/v) with respect to the volume of the composition;
      ii) said liquid composition comprises potassium bicarbonate in an amount from 2.0 to 10.0% (w/v) with respect to the volume of the composition; and
      iii) sodium is absent or present in an amount of up to 0.05% by weight with respect to the volume of the composition.

2. The method of claim 1, wherein said diclofenac potassium salt is present in said composition in an amount of about 5% (w/v) with respect to the volume of the composition.

3. The method of claim 1, or 2, wherein said potassium bicarbonate is present in said composition in an amount from 2.0 to 5.0% (w/v) with respect to the volume of the composition.

4. The method of claim 1, 2, or 3, wherein said composition has a density of from 1.0 to 1.1 g/ml.

5. The method of claim 1, 2, 3 or 4, wherein said composition further comprises at least one sweetener substantially free of sodium ions.

6. The method of claim 1, 2, 3, 4, or 5, wherein said composition further comprises from 0.3 to 2.0% (w/v) of a sweetener substantially free of sodium ions with respect to the volume of the composition.

7. The method of claim 1, 2, 3, 4, 5, or 6, wherein said composition further comprises a sweetener selected from the group consisting of sucralose, aspartame, thaumatin, isomalt, maltitol, lactitol, and xylitol.

8. The method of claim 1, 2, 3, 4, 5, 6, or 7, wherein said glycerol is present in an amount from 10 to 50% (w/v) with respect to the volume of the composition.

9. The method of claim 1, wherein said composition comprises:
   a) about 5 weight parts diclofenac potassium,
   b) about 30 weight parts ethyl alcohol,
   c) about 20 weight parts glycerol,
   d) about 2.5 weight parts potassium hydrogen carbonate,
   e) about 0.5 weight parts sucralose,
   f) about 42.9 weight parts water; and
   g) optionally about 0.00336 weight parts E129 and about 0.000168 weight parts E133.

10. The method of claim 9 wherein said composition has a density of between 1.0 and 1.1 g/ml.

11. The method of claim 1, 2, 3, 5, 6, 7, 8, 8, or 10, further comprising dispensing said composition to a vial containing from about 10 to about 100 mg of said diclofenac potassium.

12. The method of claim 1, further comprising mixing dye Allura Red (E129) and Brilliant Blue (E133) in step (c) to make said third mixture.

13. The method of claim 1, wherein:
   a) step (a) is carried out with 120 weight parts ethanol per 20 weight parts potassium diclofenac;
   b) step (b) is carried out with 80 weight parts glycerol and 120 weight parts water per 20 weight parts potassium diclofenac;
   c) step (c) is carried out with 56.6 weight parts water, 10 weight parts potassium hydrogen carbonate, and 2 weight parts sucralose per 20 weight parts diclofenac potassium; and
   d) water is added in step (d) until a 5% w/v solution is obtained based on the weight of potassium diclofenac at a density of approximately 1.030 g/mL.

14. The method of claim 1, further comprising mixing 0.01344 weight parts dye Allura Red (E129) and 0.00067 weight parts Brilliant Blue (E133) in step (c) to make said third mixture.

15. The method of claim 1, wherein said potassium bicarbonate is present in said composition in an amount of from 2.5 to 3.0% (w/v) with respect to the volume of the composition.

* * * * *